United States Patent [19]

Reynaud et al.

[11] Patent Number: 5,797,748
[45] Date of Patent: Aug. 25, 1998

[54] TOOTH PROSTHESIS WITH DIRECTIONAL DISTRIBUTION OF THE STRESS RESISTANCE AND METHOD

[75] Inventors: Marc Reynaud, 23, avenue Plaine Fleurie, 38240 Meylan; Pierre-Luc Reynaud, 9, rue du Rif-Tronchard, 38120 Saint-Egreve; Manh Chu, Saint-Egreve, all of France

[73] Assignees: Marc Reynaud, Meylan; Pierre-Luc Reynaud, Saint Egreve, both of France

[21] Appl. No.: 894,435

[22] PCT Filed: Mar. 1, 1996

[86] PCT No.: PCT/FR96/00330

§ 371 Date: Aug. 20, 1997

§ 102(e) Date: Aug. 20, 1997

[87] PCT Pub. No.: WO96/26687

PCT Pub. Date: Sep. 6, 1996

[30] Foreign Application Priority Data

Mar. 1, 1995 [FR] France .................. 95 02362

[51] Int. Cl.$^6$ ........................ A61C 5/08
[52] U.S. Cl. ........................ 433/224; 433/220
[58] Field of Search ................ 433/224, 220

[56] References Cited

U.S. PATENT DOCUMENTS

| | | | |
|---|---|---|---|
| 1,649,508 | 11/1927 | Carmichael | 433/224 |
| 3,318,000 | 5/1967 | Paris | 433/224 |
| 5,074,792 | 12/1991 | Bernadat | 433/224 |
| 5,165,893 | 11/1992 | Thompson | 433/224 |
| 5,409,378 | 4/1995 | Pohl | 433/224 |
| 5,564,929 | 10/1996 | Alpert | 433/224 |

FOREIGN PATENT DOCUMENTS

| | | |
|---|---|---|
| 0 385 892 | 9/1990 | European Pat. Off. . |
| 0 432 001 | 6/1991 | European Pat. Off. . |
| 2 588 181 | 4/1987 | France . |
| 2 626 167 | 7/1989 | France . |
| 220491 | 8/1924 | United Kingdom ........ 433/224 |

*Primary Examiner*—John J. Wilson
*Attorney, Agent, or Firm*—Young & Thompson

[57] ABSTRACT

The present invention relates to a tooth prothesis made of composite material and to a process for fabricating said prothesis. The prothesis is characterized in that it is comprised of a central core (3), made of at least one bunch of fibers (5), for example glass fibers, the core being wrapped by a sheath (7) comprised of at least one layer of oriented, isotropic or non isotropic fibers (8a, 8b, 8c) , the fibers (5) of the central core (3) and the fibers of the sheath (7) being embedded in a curable resin, the fibers (8a, 8b, 8c) of the sheath (7) being oriented in a given angle with respect to the longitudinal axis (yy') of the prothesis (1), so as to adjust to desired respective values the longitudinal and transverse traction resistance of the prothesis (1).

11 Claims, 3 Drawing Sheets

TOOTH PROSTHESIS WITH DIRECTIONAL DISTRIBUTION OF THE STRESS RESISTANCE AND METHOD

BACKGROUND OF THE INVENTION

The present invention relates to a dental prosthesis and more particularly a prothesis made of composite material adapted to control the directional distribution of the mechanical stress resistance exerted thereon. The present invention also concerns a method for manufacturing such a dental prothesis.

DESCRIPTION OF THE RELATED ART

It is known that, when a depulped tooth is reconstituted, it is essential to ensure the perennity of the residual dental substance, which is usually done by means of metal protheses, made of precious alloy or not, which are screwed or sealed in the dental canal.

It is also known that the great differences which exist between the mechanical characteristics of these metal protheses and the dentin of the tooth are the cause of most of the failures which occur in this type of intervention and which are translated by unsealings and/or cracks in the roots under the action of considerable stresses generated by the forces of chewing.

It has been proposed to overcome these drawbacks by replacing the metal protheses by protheses made of composite material, essentially constituted by carbon fibers disposed longitudinally along the axis of the prothesis which are embedded in a hardenable resin. Although the protheses of this type have overcome the principal drawbacks associated with metal protheses, nonetheless they are not totally satisfactory as their mechanical characteristics and in particular their maximum stress resistance, are the same whatever the applications envisaged.

Another drawback of this latter type of protheses is that, the carbon fibers being electrically conducting, the prothesis may constitute an electrode, vehicle of electrochemical corrosion.

Furthermore, tenons of this type employing carbon fibers are black in color, which limits their use in certain cases of aesthetic restoration.

The morphological studies carried out on the axes of insertion of the teeth in the mandibles have demonstrated that the angles of the occlusal stresses exerted thereon vary considerably. In fact, during chewing, the teeth are subjected to stresses which are applied thereon in various angular ranges and which depend in particular on the angles formed by the axes of insertion of the antagonistic teeth which meet.

In this way, for single-root teeth, these axes of insertion merge most of the time with the canal axes along which are inserted the protheses which will serve to reinforce the reconstituted teeth. For multi-root teeth, and more particularly for the molars, the canal axes of the different roots being divergent, it is known that it is no longer solely the axes of insertion of the teeth which will intervene in the stresses undergone thereby, but the different cusp slopes, the ridges, the cavities, in other words the anatomy of the triturating face, which will determine the angle of application of the occlusal forces to which the prothesis is subjected.

BRIEF DESCRIPTION OF THE INVENTION

The present invention has for its object to propose a means for making protheses of which the direction of the privileged axes of mechanical resistance may be adjusted to desired values, as a function of the direction of the stresses to which they are subjected and which depend on the type of teeth in which they are inserted.

The present invention thus has for its object a dental prothesis made of composite material, characterized in that it is constituted by a central core made of at least one bundle of fibers which is surrounded by a sheath constituted by at least one layer of fibers, isotropic or not, the fibers of the central core and those of the sheath being embedded in a hardenable resin, and the fibers of the sheath being oriented by a given angle with respect to the longitudinal axis of the prothesis.

In an embodiment of the invention, the sheath is constituted by at least two superposed layers of fibers, disposed symmetrically with respect to the longitudinal axis of the prothesis, the said two layers being able to be woven.

In a variant embodiment of the invention, the sheath is constituted by at least one layer of transverse fibers.

In an embodiment of the invention, the sheath is coated with a thin envelope comprising retention cavities, this envelope being in particular able to be constituted by a layer of non-contiguous fibers, and in particular longitudinal or transverse unidirectional fibers.

The present invention also has for its object a method of manufacturing a dental prothesis made of composite material, characterized in that it comprises the steps consisting in:

making a central core comprising at least one bundle of longitudinal fibers, arranging around the central core a peripheral sheath constituted by at least one layer of fibers oriented by a given angle with respect to the longitudinal axis of the prosthesis, arranging in a mold the central core coated with its sheath, and impregnating these two elements with a hardenable resin.

BRIEF DESCRIPTION OF THE DRAWINGS

A form of embodiment of the present invention will be described hereinafter by way of non-limiting example, with reference to the accompanying drawing, in which.

DESCRIPTION OF THE PREFERRED EMBODIMENTS

Figure 1:
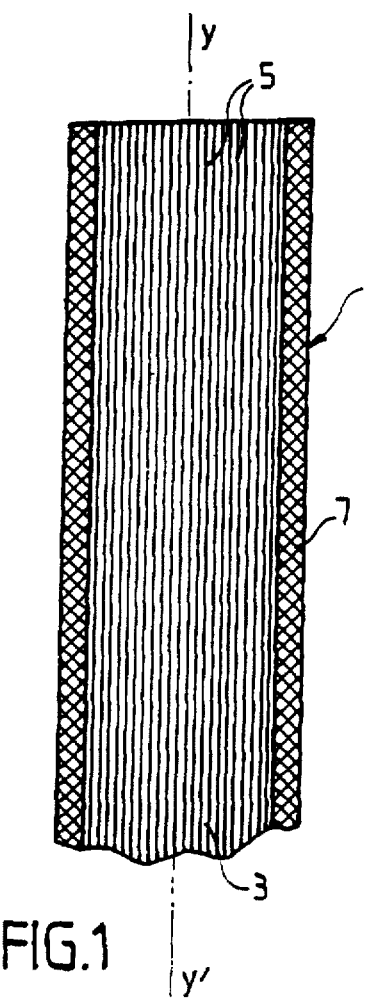
FIG. 1 is a view in partial axial and longitudinal section of a first embodiment of a prothesis according to the invention.

According to FIG. 1, a prothesis 1 according to the invention is constituted by a core 3 formed by fibers 5 of which the mechanical characteristics are isotropic (such as for example glass fibers) or anisotropic (such as for example aramide or carbon fibers) which are distributed longitudinally along axis yy' of the prothesis 1, substantially at the centre thereof, and which are embedded in a matrix of hardenable resin such as for example an epoxy resin.

Around the central core 3, the prothesis 1 according to the invention comprises a sheath 7 constituted by fibers with isotropic mechanical characteristics such as for example glass fibers, or fibers with anisotropic mechanical characteristics such as aramide or carbon fibers. The characteristics of the fibers constituting the sheath 7, as well as their arrangement thereinside, are a function of the privileged direction of the stress resistance which it is desired to give the prothesis 1.

In an embodiment of a first type of prothesis according to the invention, the central core 3 is formed by isotropic fibers 5, namely glass fibers, with a diameter D1+14 µm and which represent 50% of the overall volume thereof.

Figure 2:
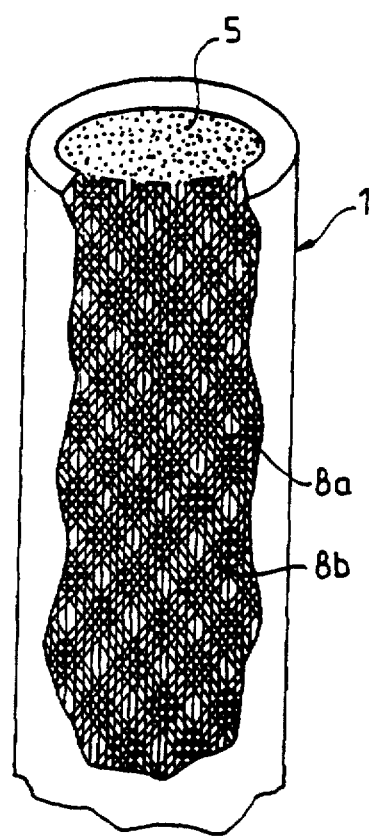
FIG. 2 is a view in partially exploded perspective of the prothesis shown in FIG. 1.
Figure 3:
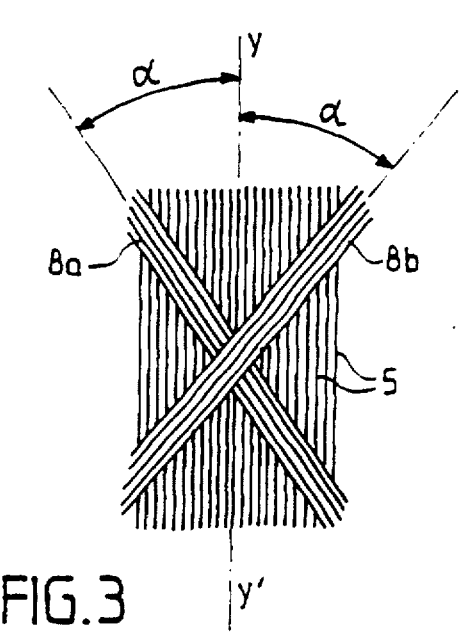
FIG. 3 is a partial schematic view of the outer sheath of the prothesis shown in FIGS. 1 and 2.

As for the peripheral sheath 7, as shown in FIGS. 2 and 3, it is constituted by two series of glass fibers 8a and 8b respectively of diameter D2=10 µm, which are disposed symmetrically with respect to the axis yy' of the prothesis 1 and which form with respect thereto angles α of 40°, namely a first series of fibers 8a which are wound around the central core 3, and a second series of fibers 8b, of quality identical to the first, and which are wound therearound. These two series of symmetrical fibers represent an overall volume of about 32% of that of the prothesis 1.

Figure 5:
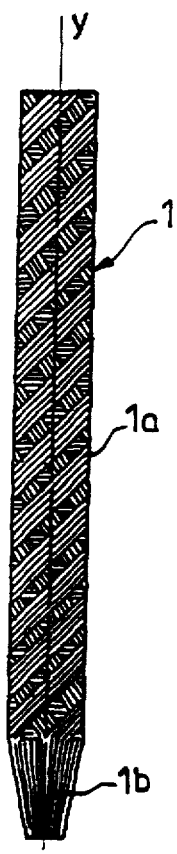
FIG. 5 is an outside view of the prothesis shown in FIGS. 1 to 4.

The characteristic shape of the prothesis 2, as shown in FIG. 5, namely a body constituted by a cylindrical part 1a followed by a truncated part 1b is obtained by machining, and particularly by turning, the outer sheath 7.

Such a prothesis presents the following mechanical characteristics (where β represents the angle of the stress with respect to the longitudinal axis of the prothesis):

longitudinal traction resistance (β=0°) 1200 MPa transverse traction resistance (β=90°) 810 MPa longitudinal modulus of elasticity in traction 41 GPa.

The present invention makes it possible to modify the longitudinal and transverse traction resistances of the prothesis 1 by simply varying the angle a by which the fibers 8a and 8b of the outer sheath 7 are wound on the core 3.

A prothesis 1 of the same type has thus been produced, of which all the characteristics of the fibers as well as their arrangement are identical to the values of those used in the preceding example, but in which the inclination α of the fibers 8a and 8b of the outer sheath 7 is less and presents a value of 25°.

The mechanical characteristics of such a prothesis are then as follows:

longitudinal traction resistance (β=0°) 1310 MPa transverse traction resistance (β=90°) 690 MPa longitudinal modulus of elasticity in traction 49 GPa.

It is thus ascertained that this second prothesis 1 presents a better traction resistance in the longitudinal direction than the first, while its transverse traction resistance is lower. The second prothesis is thus more suitable for use in relation with dental canals., or teeth cavities, in which the preferential direction of the stresses is essentially longitudinal. Such is the case in particular when the prothesis is fixed in second premolars.

On the other hand, when the efforts have a transverse preferential component, the first prothesis is more efficient than the second. Such is the case in particular when the prothesis is fixed in incisives or canines.

Figure 4:
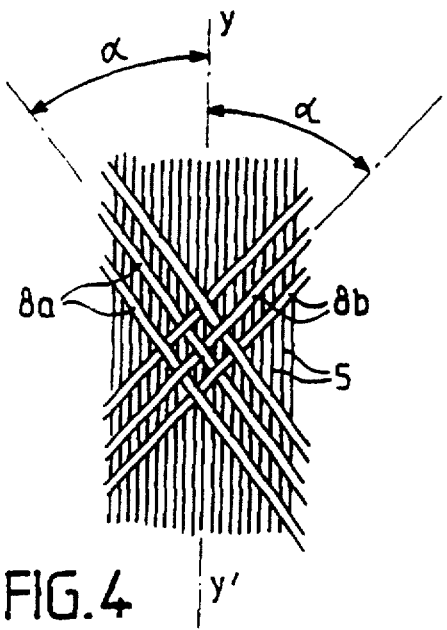
FIG. 4 is a partial schematic view of a variant embodiment of the sheath shown in FIG. 3.
Figure 6:
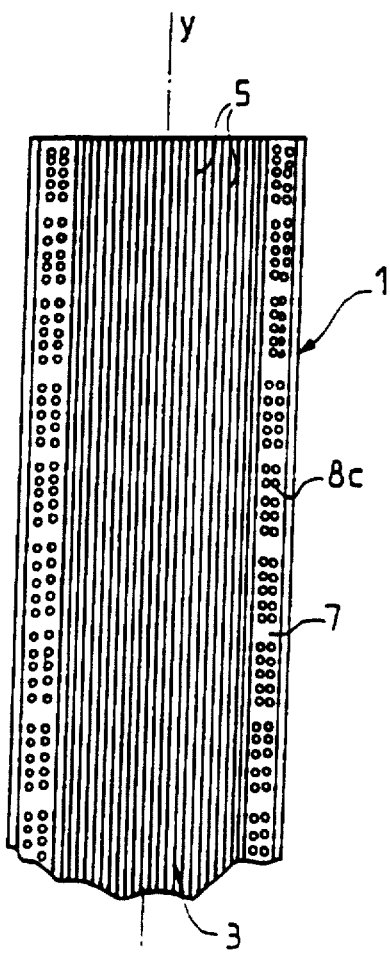
FIG. 6 is a view in partial axial and longitudinal section of a second embodiment of a prothesis according to the invention.
Figure 7:
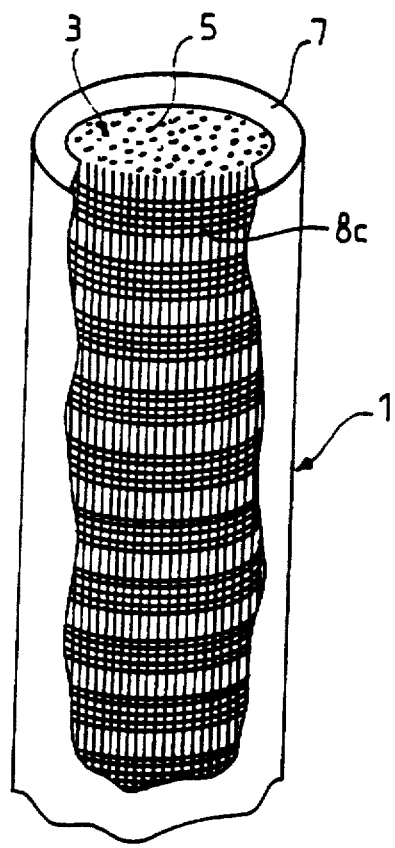
FIG. 7 is a view in partially exploded perspective of the prothesis shown in FIG. 6.
Figure 8:
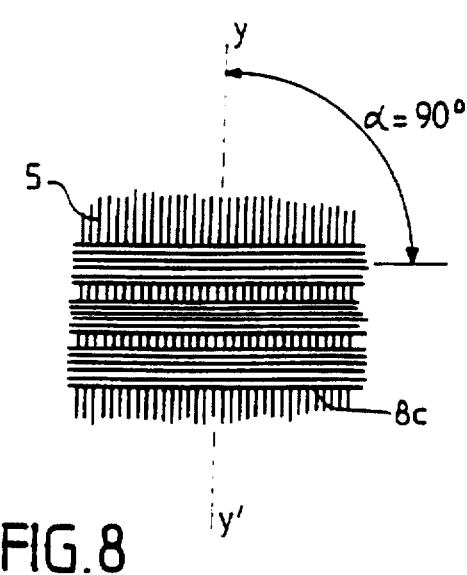
FIG. 8 is a partial schematic view of the outer sheath of the prothesis shown in FIGS. 6 and 7.

As shown in FIG. 4, fibers 8a and 8b which form a woven web may also be used for constituting the sheath 7, the angle α formed by these fibers with the longitudinal axis yy' of the prothesis 1 being determined as set forth hereinbefore. This web may be woven around the central core or, preferably, be made previously so as to constitute a sheath in which the central core is introduced.

FIGS. 6 to 9 show a variant embodiment of a prothesis according to the invention intended to constitute an intradentine prothesis, i.e. a prothesis which is subjected to stresses which are essentially perpendicular to its longitudinal axis.

This prothesis 2 is also constituted by a core 3 formed by quartz fibers 5 of diameter D3=9 µm which are embedded in a matrix of epoxy resin and which represent about 35% of the overall volume of the prothesis 1.

The sheath 7 is also constituted by quartz fibers 8c of the same diameter, which are wound on the core 3 perpendicularly to the longitudinal axis yy' thereof (α=90°) and which occupy about 40% of the overall volume of the prothesis 1.

The mechanical characteristics of such a prothesis are as follows:

longitudinal traction resistance (β=0°) 1050 MPa transverse traction resistance (β=90°) 950 MPa longitudinal modulus of elasticity in traction 45 GPa.

It is ascertained that this prothesis presents a mechanical traction resistance in the transverse direction very close to its traction resistance in the longitudinal direction, which renders it particularly suitable for constituting intradentine prothesiss.

Figure 10:
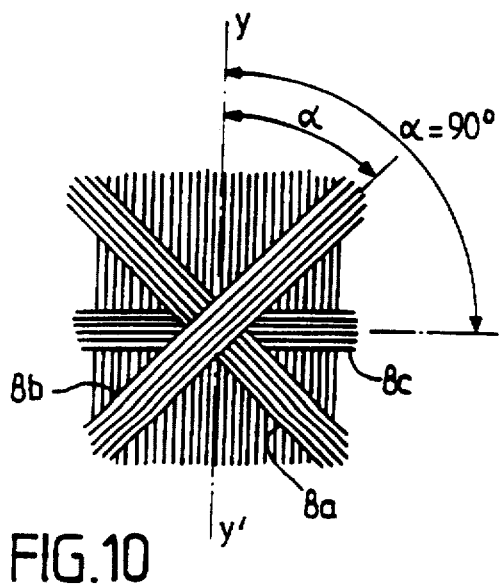
FIG. 10 is a partial schematic view of a variant embodiment of the sheath shown in FIG. 8.

As shown in FIG. 10, a sheath 7 may also be made, constituted by three layers of fibers, namely a first layer constituted by transverse fibers 8c (α=90°), coated with two layers 8a and 8b which are symmetrical with respect to the longitudinal axis yy' of the prothesis and which form with respect thereto given angles α of 45°.

The core 3 of this prothesis is formed by the same fibers used in the previous example, the volumes of the core 3 and of the sheath 7 representing respectively 35% and 40% of the overall volume of the prothesis 1.

In this example, the volume of the transverse fibers is about 20% of the overall volume of the prothesis 1.

The mechanical characteristics of such a prothesis are as follows:

longitudinal traction resistance (β=0°) 1300 MPa transverse traction resistance (β=90°) 930 MPa longitudinal modulus of elasticity in traction 47 GPa.

This embodiment has made it possible, as shown in the preceding Table, to improve the longitudinal traction resistance (this traction resistance passed from 1050 MPa to 1300 MPa) while decreasing by only a small value the transverse traction resistance (this latter having passed from 950 MPa to 930 MPa).

In order to constitute the peripheral sheath 7 of the prothesis 2, fibers presenting anisotropic mechanical characteristics such as for example aramide fibers, may of course be used. In a prothesis constituted as described in Example 2, the glass fibers of the outer sheath have thus been replaced by aramide fibers. The mechanical characteristics of the prothesis thus obtained are as follows:

longitudinal traction resistance (β=0°) 1280 MPa transverse traction resistance (β=90°) 750 MPa longitudinal modulus of elasticity in traction 55 GPa.

The embodiment is particularly advantageous for applications in which the longitudinal resistance is the major characteristic, which is particularly the case for root prothesiss.

Figures 9, 11:
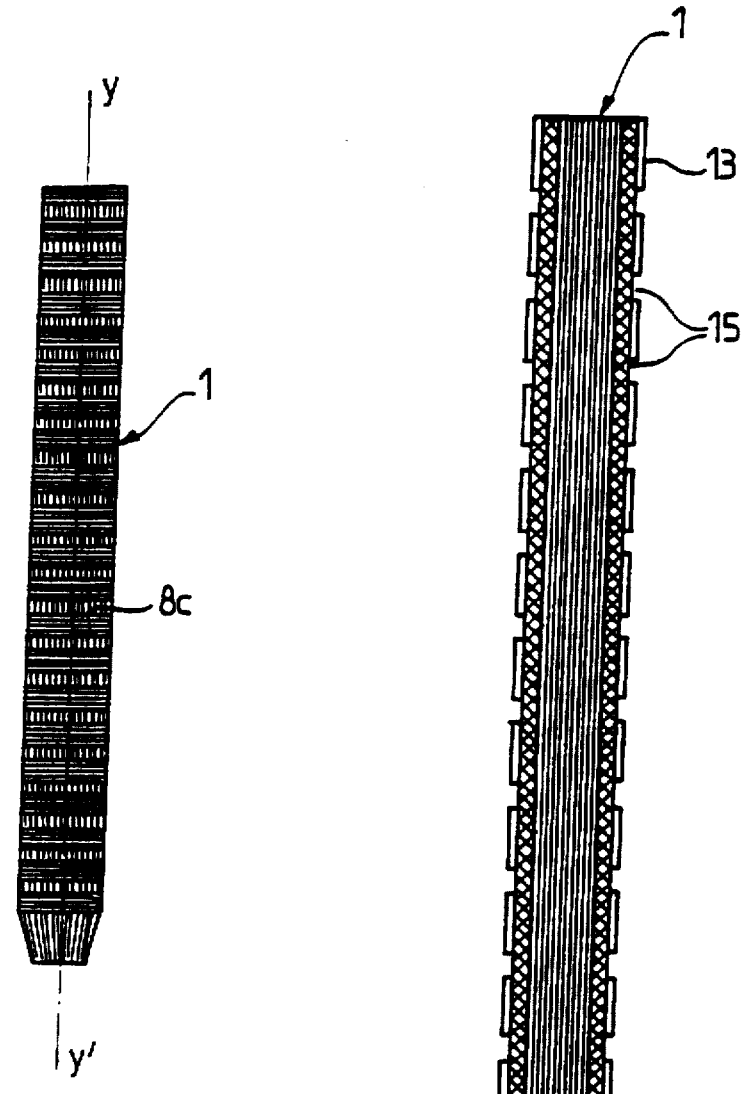
FIG. 9 is an outer view of the prothesis shown in FIGS. 6 to 8.
FIG. 11 is an outside view of a variant embodiment of a prothesis according to the invention.

As shown in FIG. 11, and in order to facilitate adhesion of the protheses according to the invention with the cements used in the dental art, macroretentions may be created on the surface thereof, in the sheath 7, particularly by machining, and more particularly by turning or slicing. In order to avoid deteriorating the sheath 7, which would have for its effect to modify the mechanical characteristics of the prothesis, the sheath is overmolded with a resin envelope 13 of small thickness, for example of the order of some tenths of millimeters, and the macro-retentions, for example circular grooves, are created in this resin.

When the small diameter of certain protheses, such as for example intradentin protheses, renders such an embodiment virtually impossible, the envelope is made by means of longitudinal or transverse unidirectional fibers in which the macro-retentions 15 are machined.

Apart from mastering the directions of greatest resistance of the prothesiss made of composite material, the present invention also improves their aesthetic character. In fact, it makes it possible to employ materials which are interesting, particularly by their color, but whose mechanical qualities are insufficient to constitute a dental prothesis, insofar as the characteristics of the core of this prothesis enable those of the sheath to be compensated.

Such a prothesis may for example be obtained by making a central core comprising at least one bundle of longitudinal fibers, by arranging around the central core a peripheral sheath constituted by at least one layer of fibers oriented by a given angle with respect to the longitudinal axis of the prothesis, by disposing the central core coated with its sheath in a mould, and by impregnating these two elements with a hardenable resin.

We claim:

1. Dental prothesis made of composite material, comprising a central core (3) made of at least one bundle of fibers (5) which is surrounded by a sheath (7) constituted by at least one layer of fibers (8a, 8b, 8c), the fibers (5) of the central core (3) and those of the sheath (7) being embedded in a hardenable resin, and the fibers (8a, 8b, 8c) of the sheath (7) being oriented by a given angle ($\alpha$) with respect to the longitudinal axis (yy') of the prothesis (1).

2. Prothesis according to claim 1, wherein at least one bundle of the fibers constituting the core of the prothesis (1) is formed by longitudinal fibers.

3. Prothesis according to claim 1, wherein the sheath (7) comprises at least two superposed layers of fibers (8a, 8b) disposed symmetrically with respect to the longitudinal axis (y, y') of the prothesis (1).

4. Prothesis according to claim 1, wherein the fibers (8a, 8b) form an angle ($\alpha$) included between 30° and 45° with the longitudinal axis (yy') of the prothesis (1).

5. Prothesis according to claim 1, wherein said layers (8a, 8b) are woven.

6. Prothesis according to any claim 1, wherein the sheath (7) comprises at least one layer of transverse fibers (8c).

7. Prothesis according to claim 1, wherein the prothesis (1) is provided on its periphery with retention means (15).

8. Prothesis according to claim 7, wherein the retention means are produced in the sheath (7).

9. Prothesis according to claim 7, wherein the sheath (7) is coated with a thin envelope (13) comprising retention cavities.

10. Prothesis according to claim 9, wherein the envelope is constituted by a layer of longitudinal unidirectional fibers.

11. Method for manufacturing a dental prothesis of composite material, comprising the steps:

producing a central core comprising at least one bundle of longitudinal fibers, arranging around the central core a peripheral sheath constituted by at least one layer of fibers oriented by a given angle ($\alpha$) with respect to the longitudinal axis (yy') of the prothesis (1), arranging the central core coated with its sheath in a mold, and impregnating these two elements with a hardenable resin.

* * * * *